(12) United States Patent
Merette et al.

(10) Patent No.: US 12,201,368 B2
(45) Date of Patent: *Jan. 21, 2025

(54) METHOD AND SYSTEM FOR PRE-OPERATIVE IMPLANT SIZING

(71) Applicant: ORTHOSOFT ULC, Montreal (CA)

(72) Inventors: Jean-Sebastien Merette, Mont-St-Hilaire (CA); Ramnada Chav, Laval (CA)

(73) Assignee: ORTHOSOFT ULC, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/166,186

(22) Filed: Feb. 8, 2023

(65) Prior Publication Data

US 2023/0181259 A1 Jun. 15, 2023

Related U.S. Application Data

(63) Continuation of application No. 17/064,653, filed on Oct. 7, 2020, now Pat. No. 11,583,341, which is a continuation of application No. 16/156,436, filed on Oct. 10, 2018, now Pat. No. 10,828,110.

(60) Provisional application No. 62/570,361, filed on Oct. 10, 2017.

(51) Int. Cl.
*A61B 34/10* (2016.01)
*A61B 90/00* (2016.01)

(52) U.S. Cl.
CPC .............. *A61B 34/10* (2016.02); *A61B 90/37* (2016.02); *A61B 2034/102* (2016.02); *A61B 2034/105* (2016.02); *A61B 2034/108* (2016.02)

(58) Field of Classification Search
CPC .............. A61B 34/10; A61B 2034/101; A61B 2034/102; A61B 2034/105; A61B 2034/107; A61B 2034/108; A61B 90/37
See application file for complete search history.

(56) References Cited

U.S. PATENT DOCUMENTS

| | | | | |
|---|---|---|---|---|
| 9,861,446 B2 * | 1/2018 | Lang | ................... | A61B 17/1775 |
| 9,980,780 B2 * | 5/2018 | Lang | ................... | A61F 2/32 |
| 10,143,533 B2 * | 12/2018 | Park | ................... | G06T 7/60 |
| 10,159,530 B2 * | 12/2018 | Lang | ................... | A61F 2/389 |
| 10,278,777 B1 * | 5/2019 | Lang | ................... | A61B 90/36 |
| 10,292,768 B2 * | 5/2019 | Lang | ................... | H05K 999/99 |

(Continued)

*Primary Examiner* — Eric S Gibson
(74) *Attorney, Agent, or Firm* — NORTON ROSE FULBRIGHT CANADA LLP

(57) ABSTRACT

A system for sizing an implant for a patient pre-operatively comprises a processor unit. A non-transitory computer-readable memory may be communicatively coupled to the processing unit and comprising computer-readable program instructions executable by the processing unit for obtaining at least one radiographic patient image of at least one patient bone with a scale marker relative to the bone, the scale marker having a known geometry, setting a scale of the at least one radiographic patient image using the known geometry of the scale marker, generating a three-dimensional bone model representative of the at least one patient bone using the at least one radiographic patient image and the scale, identifying an implant size and/or an implant model using implant models and dimensions of the three-dimensional bone model based on said scale, and outputting the implant size and/or the implant model for the patient.

16 Claims, 7 Drawing Sheets

(56) References Cited

U.S. PATENT DOCUMENTS

| | | | |
|---|---|---|---|
| 10,368,947 B2* | 8/2019 | Lang | A61B 17/1778 |
| 10,405,927 B1* | 9/2019 | Lang | A61B 90/36 |
| 10,420,614 B2* | 9/2019 | Bell | A61B 6/505 |
| 10,603,113 B2* | 3/2020 | Lang | A61B 90/37 |
| 10,828,110 B1* | 11/2020 | Merette | A61B 90/37 |
| 11,583,341 B2* | 2/2023 | Merette | A61B 90/37 |
| 2004/0086082 A1* | 5/2004 | Foos | A61B 5/1072 378/163 |
| 2013/0266124 A1* | 10/2013 | Coursolle | A61B 90/39 378/163 |
| 2017/0258526 A1* | 9/2017 | Lang | A61B 17/1775 |
| 2017/0340391 A1* | 11/2017 | Bell | A61B 6/0492 |
| 2018/0098820 A1* | 4/2018 | Park | G06T 7/55 |
| 2018/0116728 A1* | 5/2018 | Lang | A61B 17/155 |
| 2018/0125584 A1* | 5/2018 | Lang | A61B 17/155 |
| 2018/0263704 A1* | 9/2018 | Lang | A61B 90/36 |
| 2019/0110842 A1* | 4/2019 | Lang | A61B 17/1778 |
| 2019/0192226 A1* | 6/2019 | Lang | A61B 17/1703 |
| 2019/0262078 A1* | 8/2019 | Lang | A61B 90/37 |
| 2019/0380784 A1* | 12/2019 | Lang | A61B 17/1703 |
| 2020/0060767 A1* | 2/2020 | Lang | A61B 17/1742 |
| 2020/0138518 A1* | 5/2020 | Lang | A61B 34/10 |
| 2021/0015556 A1* | 1/2021 | Merette | A61B 90/37 |
| 2023/0181259 A1* | 6/2023 | Merette | A61B 90/39 606/102 |

* cited by examiner

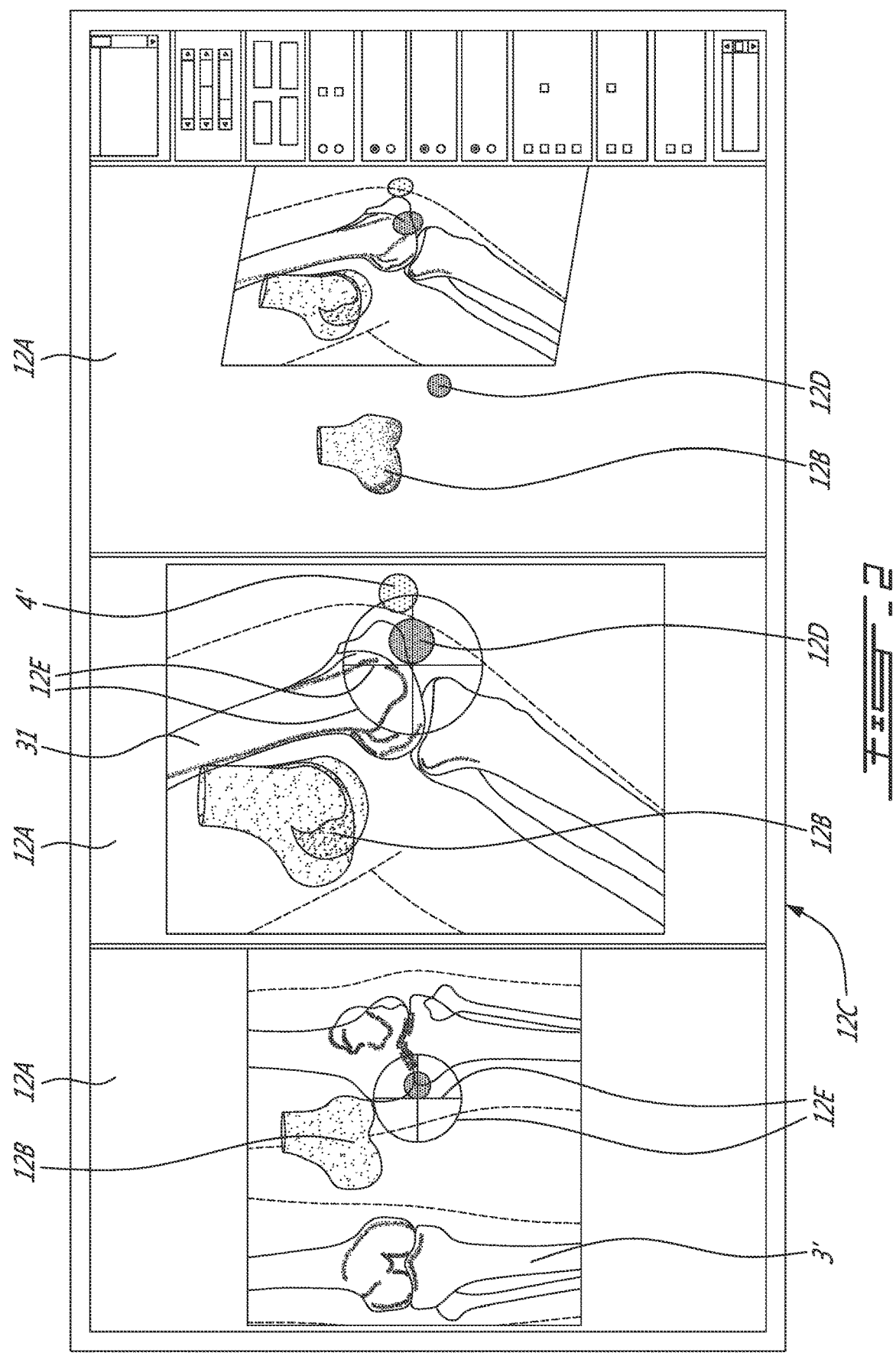

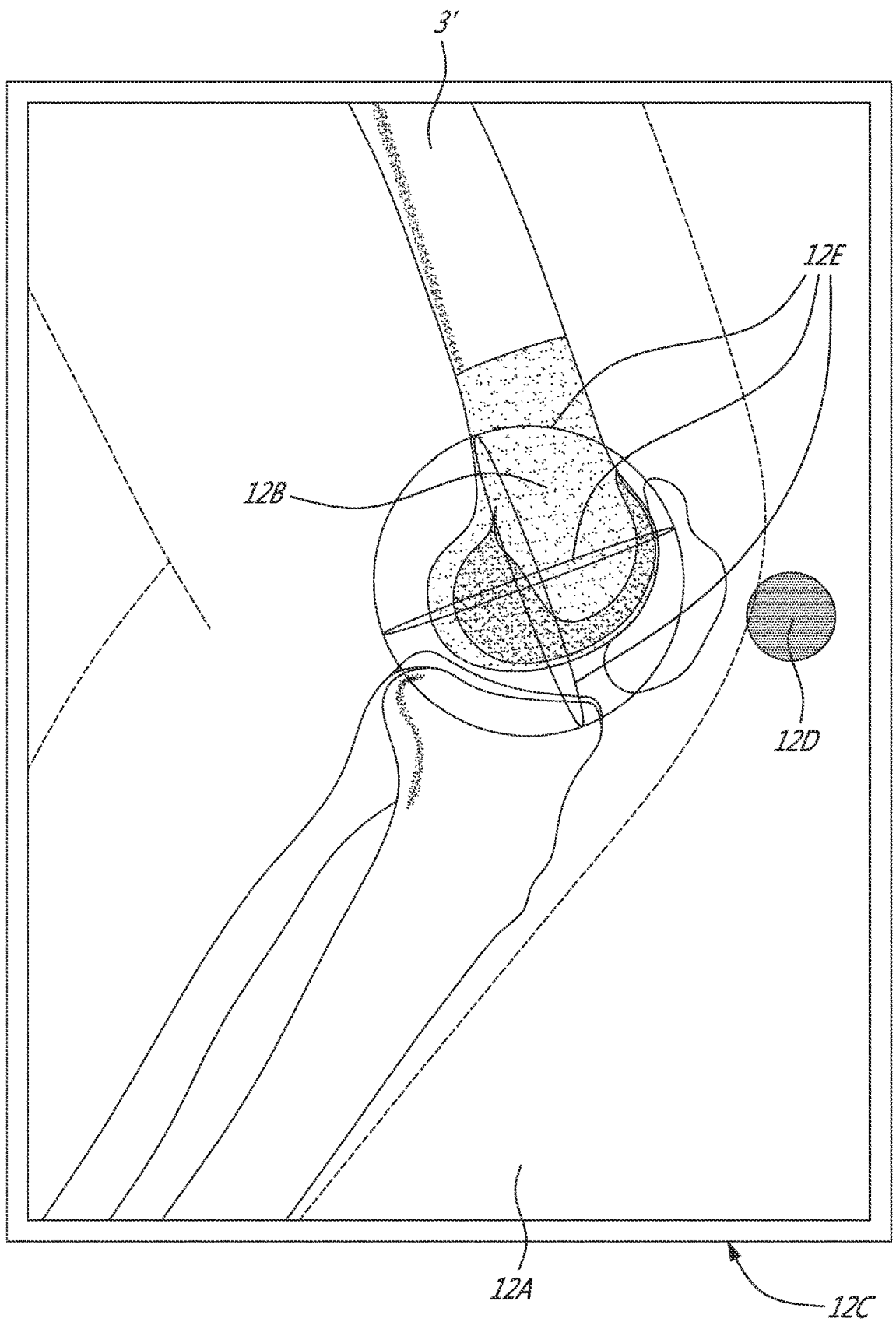

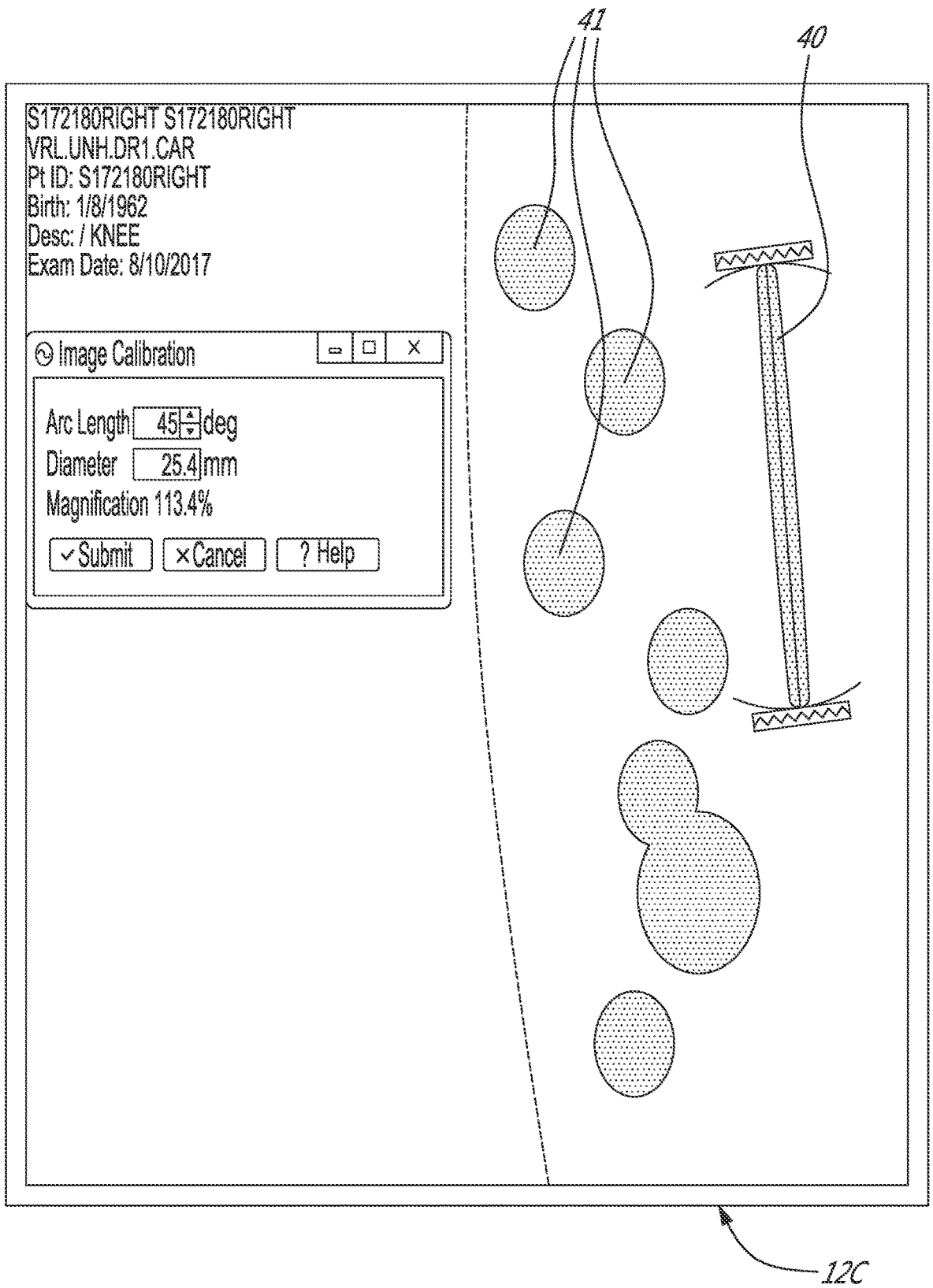

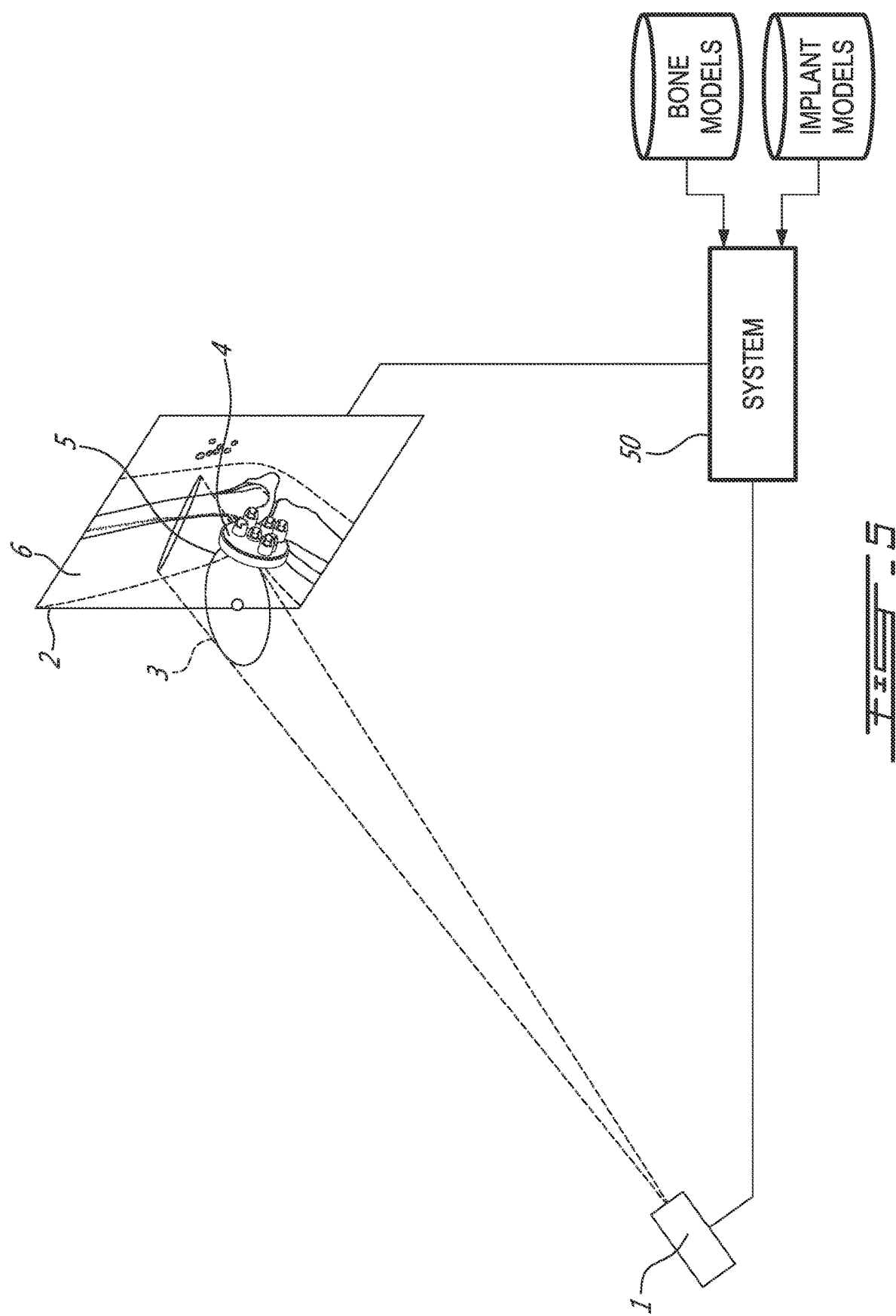

METHOD AND SYSTEM FOR PRE-OPERATIVE IMPLANT SIZING

CROSS-REFERENCE TO RELATED APPLICATION

The present application is a continuation of U.S. patent application Ser. No. 17/064,653, filed on Oct. 7, 2020 which is a continuation of U.S. patent application Ser. No. 16/156,436, filed on Oct. 10, 2018, which claims the priority of U.S. Patent Application No. 62/570,361, filed on Oct. 10, 2017 and incorporated herein by reference.

FIELD OF THE APPLICATION

The present application relates to computer-assisted surgery and, more particularly, to a pre-operative sizing of implants in the planning of surgery.

BACKGROUND OF THE ART

Radiographic imaging is commonly used to image bones and soft tissue, to detect pathologies and to plan for surgery. In particular, projectional radiography equipment may be more easily accessible than other imaging equipment. For instance, in knee orthopedic surgery, a femoral and/or tibial implant component are respectively implanted in the femur and tibia, at the knee, and the planning may often be performed using projectional X-ray images.

The X-ray images are typically obtained in projectional radiography from a lateral point of view, and from an anterior point of view. Accordingly, the X-ray images are two-dimensional (2D). Orthopedic surgery planning techniques rely on such 2D images to determine the required size of a three-dimensional (3D) implant. However, the various overlapping bone structures (e.g., the two condyles of the femur), and the difficulty in obtaining a precise lateral or anterior positioning of the imaging equipment relative to the bone, may affect an operator's ability to precisely size the bone from such images, and thus implant size planning may be improper. It is common that implant size planning done pre-operatively based on X-ray images is incorrect. As a consequence, it may be necessary for surgical operations to keep an inventory of different implant sizes with a view to address incorrect implant size planning.

SUMMARY OF THE APPLICATION

It is therefore an aim of the present application to provide a novel method and system for sizing implants pre-operatively.

It is an aim of the present application to provide a novel method and system for generating a 3D bone model sized using a 2D patient image.

Therefore, in accordance with an embodiment of the present disclosure, there is provided a system for sizing an implant for a patient pre-operatively comprising: a processor unit; a non-transitory computer-readable memory may be communicatively coupled to the processing unit and comprising computer-readable program instructions executable by the processing unit for obtaining at least one radiographic patient image of at least one patient bone with a scale marker relative to the bone, the scale marker having a known geometry, setting a scale of the at least one radiographic patient image using the known geometry of the scale marker, generating a three-dimensional bone model representative of the at least one patient bone using the at least one radio- graphic patient image and the scale, identifying an implant size and/or an implant model using implant models and dimensions of the three-dimensional bone model based on said scale, and outputting the implant size and/or the implant model for the patient.

In accordance with another embodiment of the present disclosure, there is provided a system for sizing an implant for a patient pre-operatively comprising: a processor unit; a non-transitory computer-readable memory may be communicatively coupled to the processing unit and comprising computer-readable program instructions executable by the processing unit for obtaining at least one radiographic patient image of at least one patient bone with a scale marker relative to the bone, the scale marker having a known geometry, setting a scale of the at least one radiographic patient image using the known geometry of the scale marker, matching a three-dimensional implant model with the at least one patient bone using the at least one radiographic patient image and the scale, identifying an implant size and/or an implant model and dimensions of the three-dimensional implant model based on said scale, and outputting the implant size and/or the implant model for the patient.

BRIEF DESCRIPTION OF THE DRAWINGS

FIG. 2 is a screen shot of an exemplary display used in the method of FIG. 1;

FIG. 3 is an enlarged screen shot of an exemplary display used in the method of FIG. 1, with implant plane indicators in accordance with an embodiment of the present disclosure;

FIGS. 4A to 4C are images of a scale marker in accordance with another aspect of the present disclosure; and FIG. 5 is a perspective schematic view of a computer-assisted surgery system in accordance with the present disclosure, with a scale marker and radiographic equipment.

DESCRIPTION OF THE PREFERRED EMBODIMENTS

Figure 1:
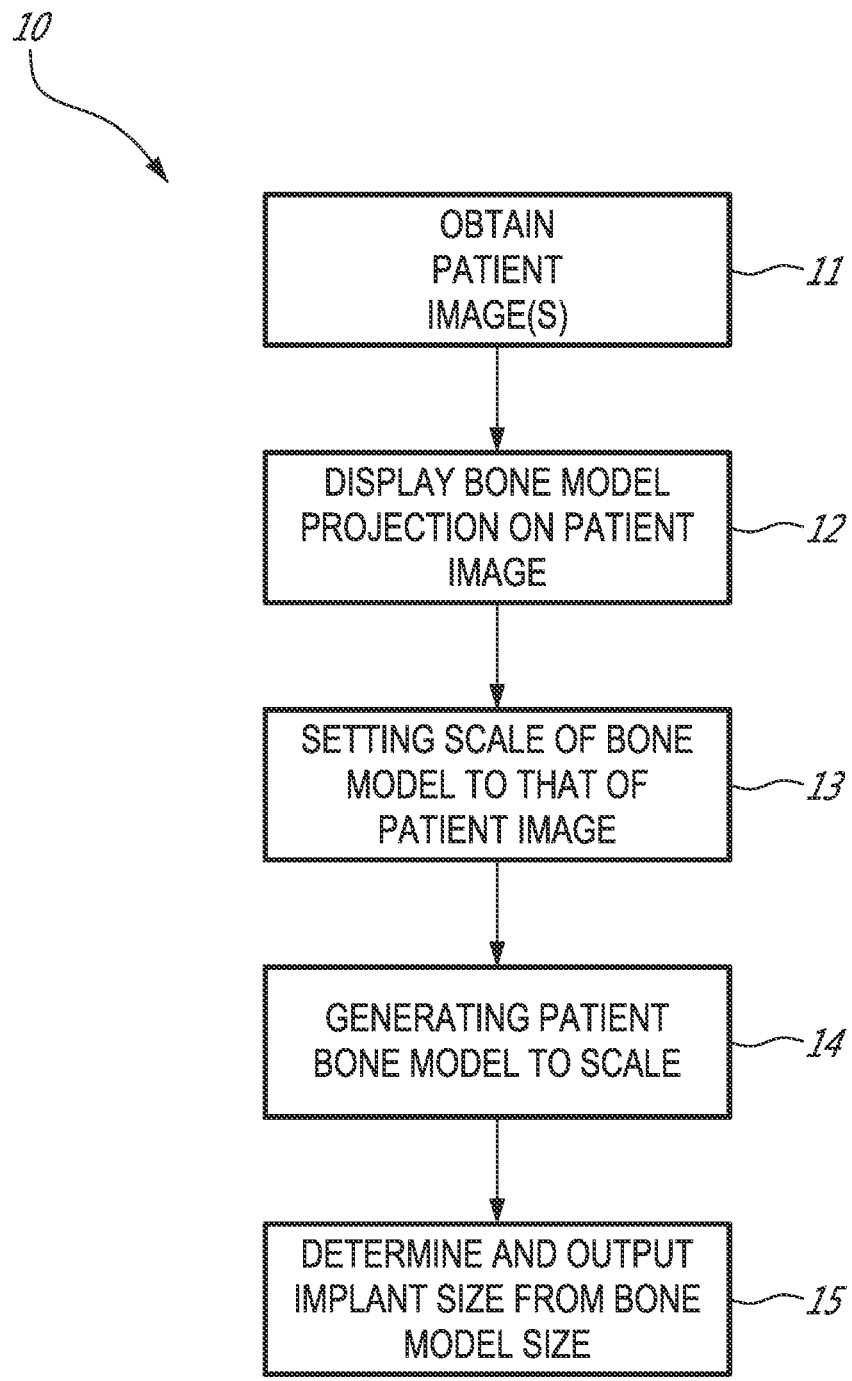
FIG. 1 is a flow chart of a method for sizing implants pre-operatively in accordance with the present disclosure.

Referring to FIG. 1, a method for sizing implants pre-operatively is generally shown at 10. The method 10 is performed in pre-operative planning, i.e., before the commencement of surgery, for an operator to obtain an implant size or implant size range specific to the patient. Reference is made herein to an example featuring the knee femur. However, the method 10 can be used to size other implants, for example a tibia implant, shoulder implants, trauma hardware, etc. The method 10 may be of the type performed by one or more processor units. A non-transitory computer-readable memory may be communicatively coupled to the processing unit and comprising computer-readable program instructions executable by the processing unit for performing the method 10.

According to 11, one or more images of a bone are obtained, referred to herein as patient image(s), as the image(s) is patient specific. The patient image may be a projectional radiographic image (also known as X-ray image), and thus be a 2D representation of the target bone and surrounding tissue and bone(s). In knee surgery, the patient images may include an image taken from a lateral point of view (including medial), i.e., a lateral image. An anterior or posterior image, taken from an anterior or posterior point of view (POV) of the radiographic equipment (a.k.a., X-ray machine), may also be obtained. The image(s)

may be in any appropriate format, such as a digital file, for digital display, and obtaining the patient image(s) may include operating the radiographic equipment, for example, to generate the images or obtaining images of a previously occurred radiography session. Other imaging equipment that may be used for 11 include fluoroscopy equipment, C-arm, CT scanner, etc. The concept of projectional radiography is shown in FIG. 5, with an X-ray generator 1 (a.k.a., X-ray source) located at a point of view and emitting X-rays. An X-ray detector 2, e.g., image plate, photographic plate, electronic detector, film, captures some of the X-rays. A bodily part, such as a limb 3, is positioned between the X-ray generator 1 and the X-ray detector 2. The limb 3 has a scale marker 4, thereon, for instance with a strap 5 to be attached to the limb 3. The limb 3 and the marker 4 block some X-rays from being reaching the X-ray detector 2, whereby the contrast 6 on the X-ray detector 2 is representative of various anatomical features having different densities and compositions. Hence, the image as obtained on the X-ray detector 2 is a projection of the limb 3 and scale marker 4 from the X-ray generator 1 onto the plane of the X-ray detector 2. FIG. 5 illustrates a trigonometric relation between the X-ray generator 1, the X-ray detector 2, the limb 3 and the scale marker 4, with values such as source-detector distance (SDD), namely the distance between the X-ray generator 1, the X-ray detector 2; source-object distance (SOD), namely the distance between the X-ray generator 1 and the limb 3; and object-detector distance (ODD), namely the distance between the limb 3 and the X-ray detector 2. The present disclosure pertains to the use of the scale marker 4 to determine the SOD and hence evaluate the actual dimensions of the bone from the images. The present disclosure may therefore determine the radiographic magnification factor (RMF) using trigonometry.

According to an embodiment, the patient image includes a projection 4' of the scale marker 4, also known as a scale reference, magnification object, etc, relative to the patient tissues, including the projection 3' of the bones of the limb 3. The scale marker 4 is present in the appropriate patient plane during the imaging, and may be made of a radio-opaque material so as to be visible in high contrast in the patient image. For example, for the lateral image, the scale marker may be positioned relative to the imaging equipment to be located to the side of the bone in the sagittal plane of the patient, and for the anterior image, the scale marker may be positioned relative to the imaging equipment to be located to the side of the bone in the frontal plane of the patient. As the dimension and the geometry (e.g., a three-dimensional geometry) of the scale marker is known, a correlation between the dimension of the scale marker and the marker dimension on the image may be used to define a depth of the scale marker in the image acquisition, i.e., a distance of the scale marker relative to the X-ray generator and/or X-ray detector. The bone landmarks may then be set to that depth, e.g., by trigonometry. The method 10, as described herein, will adjust the orientation of a bone model to the patient image. Consequently, it is not necessary that the patient be positioned in a strict point of view vis à vis the radiographic equipment (e.g., fully frontal or fully lateral), as the method 10 does this orientation adjustment.

According to 12, the patient image(s) 12A is (are) optionally displayed to the operator, along with an overlaid display of a bone model 12B. The bone model 12B is a 3D digital model that comprises at least an outer surface of a given region of a bone. For example, in FIGS. 2 and 3, the bone model 12B is a 3D virtual representation of the knee femur, with a section of femoral shaft. The images 12A and bone model 12B are displayed on any appropriate monitor, screen, tablet, etc. Referring to FIG. 2, an exemplary display screen 12C is shown, as featuring an anterior image and a lateral image on the left-hand side panel, the enlarged lateral image in the central panel, and a representation of the bone model 12B in the right-hand side panel. A single panel may suffice, such as the central panel, for performing steps of the method 10. In the display screen 12C, the bone model 12B is displaceable in a manner described hereinafter through operations performed by an operator or by a processor unit via appropriate interfaces, while the radiographic image 12A of the bone is fixed. Contrary to the radiographic image 12A, the bone model 12B may not be patient specific, and may thus be a generic bone model. The bone model 12B may for example be selected from a database, library or atlas of bone models, and may be an average patient tissue model as described in U.S. Pat. No. 9,717,508, incorporated herein by reference. Therefore, 12 may include selecting a bone model from an available source, and the selecting may be done in an automated way. A non-exhaustive list of factors influencing the selection of a bone model for the patient may include gender, age, weight, height, and/or race of the patient, among other factors. In terms of size, the bone model may be based on pre-operative measurements of landmarks taken on the patient's skin, or on an approximation of bone size, for example.

In displaying the bone model 12B as overlaid on the patient image 12A, the bone model 12B is projected as a 2D image, but with some shading representative of overlapping bone structures. In FIG. 2, the shading may be indicative of bone depressions such as the intercondylar fossa, the patellar groove, etc, according to the orientation of the 3D bone model relative to the point of view. Therefore, the method 10 may require that appropriate overlap two-dimensional rendering be performed, and this requires appropriate computational capacity. Stated differently, the method and system of the present disclosure emulate projectional X-ray images from an orientation of the bone model relative to a given point of view, the point of view for instance being that of the X-ray generator 1. Rendering updates due to variations of the orientation of the bone model relative to the point of view may be updated in real-time in the emulated projection.

The display 12C may also include the projection 4' of scale marker 4, as shown as a dot (or solid circle, as one possible embodiment) forward of the patella in FIG. 2, and being part of the radiographic image 12A. Another scale marker 12D, i.e., a virtual one in the form of a dot, located on the patella in the central panel of FIG. 2, may be associated to the bone model 12B, and serves for the alignment in depth, as described hereinafter. In an embodiment, the scale marker 12D is scaled with the bone model 12B, i.e., an enlargement of the bone model 12B results in a proportional enlargement of the scale marker 12D.

In another embodiment, the display 12C may also include implant plane indicators 12E. The plane indicators 12E are each a visual indication of a respective plane of the bone model 12B, i.e., the sagittal, frontal and transverse planes of the bone model 12B.

The plane indicators 12E may be in the form of circles (as one possible embodiment, square being another) or other lines or line patterns forming a window or like closed shape, one of which is shown in the left-hand panel, and another one being shown in the central panel. The cross in the circles is representative of a pair of circles lying in planes parallel to the line of sight. However, once the bone model 12B is rotated relative to the patient image 12A, the cross will take the shape of ellipses, as shown in FIG. 3 and as would be observed from the POV. The plane indicators 12E are indicative of the orientation of the bone model 12B relative to the patient image 12A, the orientation of the bone model 12B being navigated as the frontal, sagittal and transverse planes of the bone model 12B. The bone model 12B is thus rotated, translated in the screen planes and/or isotropically scaled by the computer-assisted surgery system in response to manipulations by an operator, via appropriate interfaces and/or widgets. A method and system as described in U.S. Pat. No. 8,908,937, incorporated herein by reference, may be used for step 12. The movements of rotation, translation and/or isotropic scaling may be performed by the computer-assisted surgery system, with a result being an alignment between bone model 12B and image 12A. The alignment may be displayed to a user, for input and adjustments by the user through the appropriate interfaces and widgets. In yet another embodiment, there is no feature of manual adjustment, and as such the implant plane indicators 12E may not be present.

According to 13, the scale of the bone model 12B is set, for instance by alignment with a scale of the patient image 12A. To obtain an appropriate sizing of the bone model 12B and of the implant, the scales of the bone model 12B and of the patient image 12A must correspond. According to an embodiment featuring the scale markers 4' and 12D for the patient image 12A and the bone model 12B, the alignment of scales is performed. To do so, a dimension of the scale marker 4' on the patient image 12A is used as indicative of a depth of the patient anatomical structure relative to imaging equipment, e.g., such as the SOD or ODD, and thus an indication of the dimensions of the anatomical features of the patient. The depth is dependent on a positioning of the scale marker 4 in the appropriate patient plane, such as in the frontal plane for an anterior POV of the imaging equipment.

The scale marker 12D for the bone model 12B is arranged to be in the same plane as it is for the patient image, for appropriate depth alignment. Therefore, if the scale marker 4 is in the sagittal plane as in the central panel of FIG. 2 and as in FIG. 3, the bone model 12B has its scale marker 12D also in its sagittal plane. The resulting depth alignment, also known as magnification, is along the medio-lateral axis of the patient image, e.g., along a vector normal to the plane of the sheet for FIG. 3. Stated differently, for the image of FIG. 3, the X-ray generator 1 and X-ray detector 2 are generally aligned with the medio-lateral axis of the patient for the image to be obtained, and magnification is performed relative to this same axis.

The size correlation of the scale markers 4 and 12D is known. For example, the scale markers 4 and 12D may be of the same size, such that an automated process for aligning the scales may entail increasing or decreasing the size of the bone model scale marker 12D until it has the same size as the projection 4' of the scale marker 4 of the patient image 12A. As a consequence of the depth alignment, the bone model 12B and the patient image 12A are to scale, and the bone model 12B will change size to be in the appropriate scale. The scale of the patient image 12A may be tied to actual bone dimensions as mentioned above, for example taken pre-operatively physically from bone landmarks, in a non-invasive or invasive manner. Other methods may be used to associate the patient image scale marker to actual patient dimensions.

As an alternative to the use of scale markers 4 and 12D, the alignment of scale may consist in using known measurements of landmarks of the target bone, and size the bone model using these known measurements. It may be required to use multiple measurements for suitable accuracy.

In 14, when the scales are set and/or aligned, the patient bone model is generated. This may include performing a visual alignment of the projection rendering of the non-patient bone model 12B on the patient image(s) 12A is adjusted. The adjustment is made through scaling, translations and rotations. The operator or the processor may for example translate and rotate the bone model projection to be superposed on the bone 3' in the patient image 12A. The superposing may include contour superposition as a first action. In FIG. 3, from the lateral image 12C, the translations would be in the sagittal plane of the patient image 12A, and thus along an anterior-posterior axis AP and/or a cranial-caudal axis CC of the patient image 12A (assumed to be generally aligned with the corresponding axes of the patient). Translation along the medio-lateral axis is fixed by marker depth and scale alignment. The rotation for contour superposing may be about the medio-lateral axis of the patient image 12A, i.e., projecting out of the sheet of FIG. 3. The plane indicators 12E may assist in showing the magnitude of rotation, along with numerical angle values as well. Rotation optimization may be performed in all three rotational degrees of freedom. These steps may be automated by the computer-assisted surgery system, for instance with an optional user adjustment input performed after the computer-assisted surgery system outputs a suggested alignment.

Still in 14, a scaling may be done, to adjust the size of the bone model 12B as a whole, i.e., an isotropic scaling of the bone model 12B relative to the scale previously set via depth alignment. Surface deformation may also be done based on the landmarks seen from the patient image. For example, surface deformation may result in the femur shaft of the bone model matching that of the patient image.

Still in 14, the cavity superposition may be also be part of the projection adjustment. The cavity superposition entails using the various shades in the patient image(s) 12A, indicative of overlapping bone features and cavities, to adjust an orientation of the bone model 12B. The adjustment of the bone model 12B is with a view to reproduce the orientation of the actual bone relative to the radiographic equipment during the imaging. In the cavity superposition, the overlap rendering—viewed as darker shades in the bone model projection—is used by the operator or processor for the shading patterns of the projected bone model to match those of the patient image 12A. This may require translations and rotations of the bone model 12B, for example rotations along the cranal-caudal axis CC of the bone model 12B and the anterior-posterior axis AP of the bone model 12B. Throughout 14, scaling and size adjustments may be made on the bone model 12B, and recorded, for the shading pattern matching. Stated differently, through rotations and scaling, the scale is maintained, such that the size of the bone model 12B relative to the scale is known throughout 14. Once a satisfactory projection adjustment is visually reached, the bone model 12B may be sized based on the scale data and correlation to landmark measurements. Hence, at the outset of 14, the method 10 and related system provide a three-dimensional bone model 12B sized to emulate the native patient bone as imaged. In accordance with another embodiment, the projection of 14 is done with an implant model instead of with the bone model. The steps described above are performed in a similar manner, though with the implant model 12B being displayed.

In 15, with the bone model sizes, or implant model sizes, a determination of the implant size is made and output. The determination may for example be automatic, with the implant size selection based on the distances defined by the reconstructed 3D model of 14. The determination of the implant size may include more than one implant size, i.e., a range of implant sizes. For example, for the femur, the antero-posterior distance between the posterior condyle and the anterior diaphysis mostly seen on lateral image may be identified automatically and used for implant selection. For the tibia, the medio-lateral distance between the medial plateau and the lateral plateau may be used for automatic implant selection.

According to an embodiment, the implant size determination includes automatically accessing a library of implant models and determining the implant model(s) and size(s) that may match the bone model size, and thus be appropriate for the patient. Hence, the determination is patient specific.

According to FIGS. 4A-C and 5, another type of scale marker 4 is shown, as an alternative to the spherical marker of FIGS. 2 and 3. The scale marker 4 of FIGS. 4 and 5 has non-symmetrical features that may be used to assist in calculating the depth in determining a scale of the patient image 12A, as detailed above for 13. In an embodiment, the scale marker 4 of FIGS. 4A-C and 5 does not have any symmetry plane. In contrast, a spherical marker 4 as depicted in other figures may not be as accurate, because of its symmetry, and this may magnify errors. For example, in FIG. 4A, the scale marker 4 has a circular ring 40, with a non-symmetrical pattern of balls 41, all radio-opaque. Accordingly, the combination of the ring 40 and balls 41 renders the assembly non-symmetrical as a whole. Other non-symmetrical features are contemplated, such as a notch in the ring 40, for example. As another embodiment, there is no ring 40, but the balls 41 are in a non-symmetrical pattern, for example without any symmetry plane. According to an embodiment, as in FIG. 4A, the scale marker 4 with non-symmetrical features is in a casing, such that the geometrical relation between the components is fixed. The scale marker 4 of FIGS. 4A-C and 5 may then be positioned on the limb 3 to image. According to an embodiment, the scale marker 4 of FIGS. 4A-C and 5 is strapped to the limb 3, such that the scale marker 4 is more or less rotatably attached to the limb 3, i.e., it may rotate about a long axis of the limb, for the center of circular ring to be manually aligned with a depth of the limb (e.g., midway through the depth of the bone).

Figure 4A:
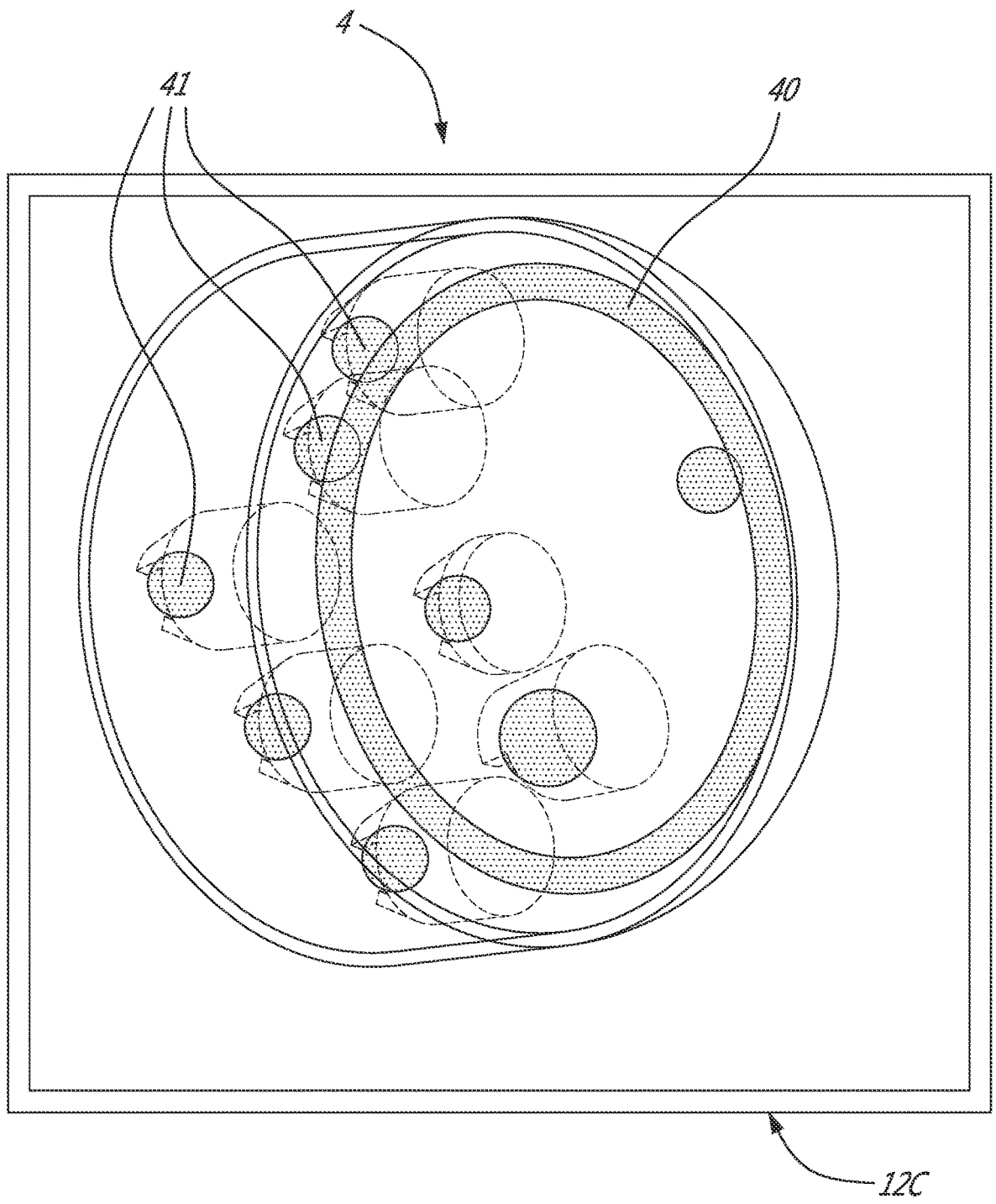

FIG. 4B shows the radiographic image of the scale marker 4 of FIG. 4A. The ring 4 is shown as being a straight line, which can be interpreted as the ring 40 being correctly centered on the depth of the limb 3 as per the pre-imaging manual positioning. As the diameter of the ring 40 is known, the depth of the patient anatomical structure relative to imaging equipment (e.g., SOD, ODD) is calculable: the height of the straight line is used to determine the depth of the center of the scale marker 4, and the center of the scale marker is at the depth SOD of the limb 3. Therefore, as in 13 above, the dimensions of the anatomical features of the patient on the image 12A are obtained. The limb 3 may be closer to the X-ray detector 2 than to the X-ray generator 1. Accordingly, the depth SOD is substantially greater than the distance from the center of the scale marker 4 to a center of the limb 3. In such an arrangement, misalignments of the scale marker 4 may lead to negligible tolerance in the calculation of the depth SOD.

Figure 4C:
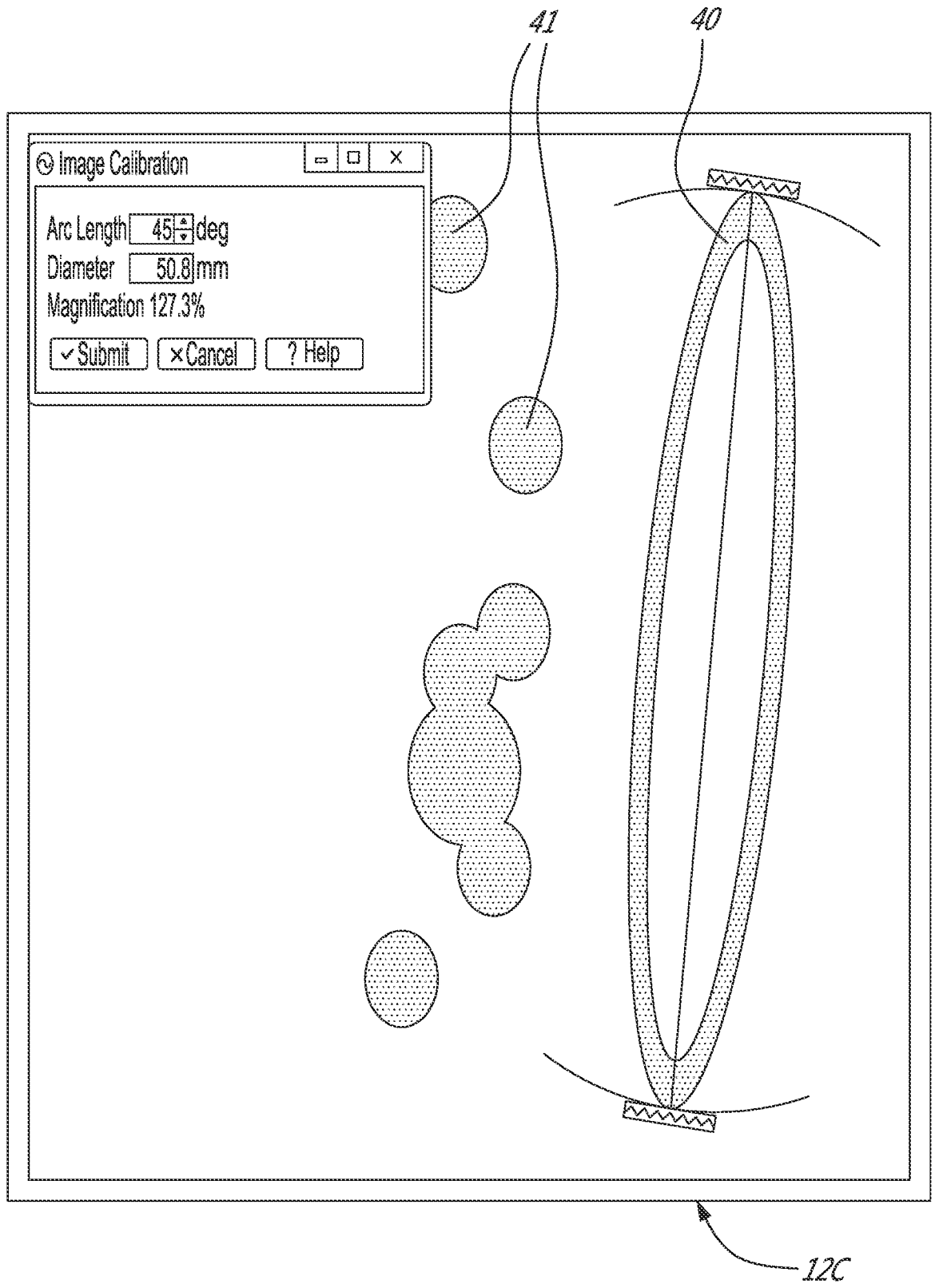

FIG. 4C also shows the radiographic image of the scale marker of FIG. 4A. The ring is shown as being an ellipse, which is an indication that the scale marker is not properly centered on the depth of the limb. The small and large diameters (d and D) of the ellipse may be used to evaluate a rotation of the scale marker off the depth of the limb: The large diameter D is used to determine the depth of the center of the ring.

The d/D ratio is a function of the angle of orientation of the ring relative to an axis of rotation (assumed to be a long axis of the limb), i.e., between 0 degree for a flat line as in FIG. 4B and $\pi/2$ for a perfect circle. In the latter case, a 90 degree rotation would be necessary to align the center of the ring with the depth. Thus, the d/D ratio gives the angle of orientation by which the center is off from the depth of the limb.

When the ring is not centered, i.e., when an ellipse is imaged, the non-symmetrical features are used to determine whether the ring is rotated rearwardly or forwardly of depth plane. The clockwise or counterclockwise direction of rotation is thus determined by the non-symmetrical feature.

The soft tissue is visible in the radiographic image, whereby the soft tissue thickness may be used to estimate the cylindricity of the limb. The angle of orientation obtained with d/D and the cylindricity are used to estimate the offset of the imaged center of the ring, from a correctly placed center of the ring. The offset provides a corrective value to adjust the depth of the image, and consequently, the scale.

Therefore, at the outset of the determination made with the image of FIG. 4C, the dimensions of the anatomical features of the patient on the image are obtained as in 13 above.

The method 10 described herein is performed by a one or more processors of a computer-assisted surgery (CAS) system. The CAS system 50 has the necessary computing capacity to perform the method 10 in real-time (or quasi real-time), especially the navigational actions 12-14, with the display screen 12C being for example part of the CAS system 50. In such steps, actions of an operator therefore result in real-time updates, for the method 10 to be interactive. The CAS system 50 has appropriate modules to perform the actions of the method 10. The CAS system 50 may have a non-transitory computer-readable memory communicatively coupled to the processing unit and comprises computer-readable program instructions executable by the processing unit. In another embodiment, the CAS system 50 includes the radiographic equipment, with the X-ray generator 1 and the X-ray detector 2.

While the method 10 is described herein as outputting an implant size, it may also be used to output one or more implant models. The method 10 may also output the 3D bone model resulting from the steps 12-14, for different uses, including subsequent determination of implant size and implant model. As additional outputs, the method 10 may produce 3D implant positioning on a 3D bone model with proposed cuts for implanting the implant, 3D implant projections on 2D X-rays, implant adjustments made by the user, for instance as 3D adjustments over 3D bone reconstruction or 2D adjustments over 2D X-Ray images.

According to an embodiment, the depth of the limb 3 may be determined using the ratio of the marker size on the image versus the marker size, to obtain a magnification factor. By knowing the distance SDD, the SOD distance, i.e., the depth of the limb 3, may be obtained. Once the depth is known, the size of the bone may be determined.

The invention claimed is:

1. A system for scaling radiographic patient imaging comprising:
   a processor unit;
   a non-transitory computer-readable memory communicatively coupled to the processing unit and comprising computer-readable program instructions executable by the processing unit for
   obtaining an overlap two-dimensional rendering of a non-patient three-dimensional bone model and a radiographic patient image of a patient bone,
   scaling the radiographic patient image by a scale factor using a scale marker in the radiographic patient image,
   generating a three-dimensional bone model representative of the patient bone by projecting the overlap two-dimensional rendering of the non-patient three-dimensional bone model on the radiographic patient image of the patient bone, and
   outputting the three-dimensional bone model representative of the patient bone.

2. The system according to claim 1, further including modifying the non-patient three-dimensional bone model using the radiographic patient image and the scale factor.

3. The system according to claim 2, wherein modifying the non-patient three-dimensional bone model includes receiving a user input of rotation, translation and/or scaling of the non-patient three-dimensional bone model.

4. The system according to claim 1, further including receiving a user input of rotation, translation and/or scaling of the overlap two-dimensional rendering, and updating in real-time the projecting of the overlap two-dimensional rendering on the radiographic patient image, based on the user input.

5. The system according to claim 1, further comprising a screen display, and wherein projecting the overlap two-dimensional rendering includes displaying the overlap two-dimensional rendering on the radiographic patient image.

6. The system according to claim 5, wherein displaying the overlap two-dimensional rendering on the radiographic patient image includes displaying the overlap two-dimensional rendering with plane indicators showing planes of the three-dimensional bone model.

7. The system according to claim 6, wherein displaying the overlap two-dimensional rendering with plane indicators representative of planes of the three-dimensional bone model includes displaying the plane indicators as lines forming a window for each plane.

8. The system according to claim 5, wherein the radiographic patient image is one of two radiographic patient images, and wherein displaying the overlap two-dimensional rendering on the radiographic patient image includes displaying the overlap two-dimensional rendering on the two radiographic patient images.

9. The system according to claim 8, wherein a first one of the two radiographic patient images is in a sagittal plane of the patient, and a second one of the two radiographic patient images is in a frontal plane of the patient.

10. The system according to claim 1, further including obtaining the non-patient three-dimensional bone model with a virtual scale marker positioned relative to the non-patient three-dimensional bone model to match an arrangement of the patient bone with the scale marker.

11. The system according to claim 10, wherein generating the three-dimensional bone model representative of the patient bone includes using the virtual scale marker with said scale factor.

12. The system according to claim 1, further comprising an X-ray generator and an x-ray detector.

13. The system according to claim 12, wherein obtaining the radiographic patient image of the patient bone includes generating the least one-radiographic patient image with the X-ray generator and the x-ray detector.

14. The system according to claim 1, wherein outputting the three-dimensional bone model representative of the patient bone includes outputting the three-dimensional bone model with an implant model overlaid onto the three-dimensional bone model.

15. The system according to claim 1, further including obtaining the non-patient three dimensional bone model from an atlas of bone models.

16. A system for scaling radiographic patient imaging into bone model comprising:
    a processor unit; and
    a non-transitory computer-readable memory communicatively coupled to the processing unit and comprising computer-readable program instructions executable by the processing unit for
    performing an overlap two-dimensional rendering of a non-patient three-dimensional bone model,
    obtaining at least one radiographic patient image of at least one patient bone with a scale marker relative to the bone, the scale marker having a known geometry,
    setting a scale of the at least one radiographic patient image using the known geometry of the scale marker,
    projecting the overlap two-dimensional rendering on the at least one radiographic patient image to generate a three-dimensional bone model representative of the at least one patient bone,
    receiving a user input of rotation, translation and/or scaling of the overlap two-dimensional rendering, and updating in real-time the projecting of the overlap two-dimensional rendering on the at least one radiographic patient image, based on the user input, and
    outputting the three-dimensional bone model representative of the at least one patient bone.

* * * * *